United States Patent
Bergins et al.

(10) Patent No.: US 10,227,901 B2
(45) Date of Patent: Mar. 12, 2019

(54) METHANATION METHOD AND POWER PLANT COMPRISING $CO_2$ METHANATION OF POWER PLANT FLUE GAS

(71) Applicant: Mitsubishi Hitachi Power Systems Europe GmbH, Duisburg (DE)

(72) Inventors: Christian Bergins, Datteln (DE); Torsten Buddenberg, Moers (DE); Emmanouil Kakaras, Dusseldorf (DE)

(73) Assignee: Mitsubishi Hitachi Power Systems Europe GMBH, Duisburg (DE)

( * ) Notice: Subject to any disclaimer, the term of this patent is extended or adjusted under 35 U.S.C. 154(b) by 100 days.

(21) Appl. No.: 14/904,033

(22) PCT Filed: Jul. 8, 2014

(86) PCT No.: PCT/EP2014/064625
§ 371 (c)(1),
(2) Date: Jan. 8, 2016

(87) PCT Pub. No.: WO2015/004143
PCT Pub. Date: Jan. 15, 2015

(65) Prior Publication Data
US 2016/0153316 A1   Jun. 2, 2016

(30) Foreign Application Priority Data

Jul. 9, 2013 (DE) .................. 10 2013 107 259
Mar. 12, 2014 (DE) .................. 10 2014 103 311
Apr. 9, 2014 (DE) .................. 10 2014 105 067

(51) Int. Cl.
*C07C 1/12* (2006.01)
*C10L 3/00* (2006.01)
(Continued)

(52) U.S. Cl.
CPC ............. *F01K 23/18* (2013.01); *C07C 1/12* (2013.01); *C07C 29/00* (2013.01); *C07C 29/152* (2013.01);
(Continued)

(58) Field of Classification Search
CPC .......... Y02E 20/14–20/366; C10L 3/00; C10L 3/06; C10L 3/08
See application file for complete search history.

(56) References Cited

U.S. PATENT DOCUMENTS 4,235,044 A   11/1980   Cheung
5,344,627 A *  9/1994   Fujii ................. B01D 53/1418
                                                          423/220

(Continued)

FOREIGN PATENT DOCUMENTS

CN   1141027 A   1/1997
CN   1318210 A   10/2001
(Continued)

OTHER PUBLICATIONS

Chinese Office Action Mar. 3, 2017 for foreign Application No. 201480049230.5.
(Continued)

*Primary Examiner* — Laert Dounis
(74) *Attorney, Agent, or Firm* — Knobbe Martens Olson & Bear LLP

(57) ABSTRACT

One embodiment relates to a methanation method comprising the conversion into methane ($CH_4$) of $CO_2$, in particular $CO_2$ gas, originating from, in particular diverted or obtained from, power plant flue gas from a power plant fired with carbon-containing fuel, in particular carbon-containing gas, and having a connected water/steam circuit, said method being performed in a methanation plant. Some embodiments provide a solution that makes it possible to couple a power
(Continued)

Figure 1:
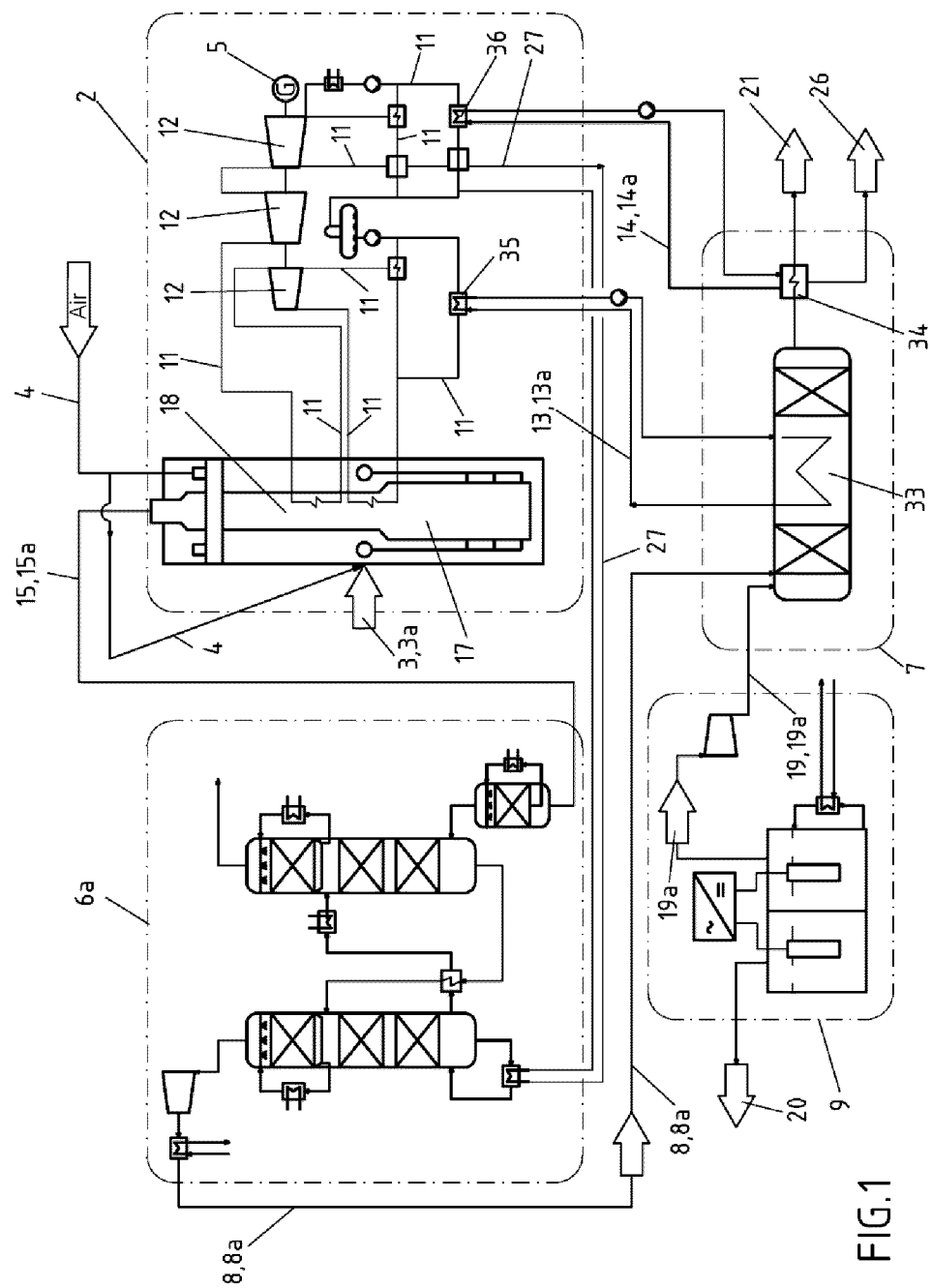

plant and a methanation plant to one another in an energetically favorable manner.

25 Claims, 9 Drawing Sheets

(51) Int. Cl.
| | |
|---|---|
| C25B 1/02 | (2006.01) |
| F01K 13/00 | (2006.01) |
| F01K 17/02 | (2006.01) |
| F01K 23/18 | (2006.01) |
| F01K 25/10 | (2006.01) |
| C25B 1/04 | (2006.01) |
| C25B 15/02 | (2006.01) |
| C25B 15/08 | (2006.01) |
| C07C 29/00 | (2006.01) |
| F01K 3/18 | (2006.01) |
| C07C 29/152 | (2006.01) |

(52) U.S. Cl.
CPC .... *C10L 3/00* (2013.01); *C25B 1/02* (2013.01); *C25B 1/04* (2013.01); *C25B 15/02* (2013.01); *C25B 15/08* (2013.01); *F01K 3/188* (2013.01); *F01K 13/00* (2013.01); *F01K 17/02* (2013.01); *F01K 25/103* (2013.01); *Y02E 20/14* (2013.01); *Y02E 20/16* (2013.01); *Y02E 20/18* (2013.01); *Y02E 20/326* (2013.01); *Y02E 60/366* (2013.01); *Y02P 20/129* (2015.11)

(56) References Cited

U.S. PATENT DOCUMENTS

| | | | |
|---|---|---|---|
| 5,416,245 A | 5/1995 | MacGregor et al. | |
| 7,244,771 B1 | 7/2007 | Seymour | |
| 2002/0095938 A1* | 7/2002 | Wintrell | F01K 25/14 60/783 |
| 2007/0130957 A1* | 6/2007 | Hoffmann | C01B 3/38 60/780 |
| 2007/0256361 A1 | 11/2007 | Kindig | |
| 2009/0247653 A1* | 10/2009 | Ravikumar | C10L 3/08 518/708 |
| 2010/0050637 A1* | 3/2010 | Yamashita | F01K 7/22 60/653 |
| 2010/0156104 A1 | 6/2010 | Bottinelli | |
| 2010/0175320 A1 | 7/2010 | Schuetzle et al. | |
| 2011/0041740 A1 | 2/2011 | Reilly | |
| 2011/0229382 A1* | 9/2011 | Frydman | C10J 3/86 422/621 |
| 2012/0091730 A1 | 4/2012 | Stuermer et al. | |
| 2012/0238645 A1 | 9/2012 | Rüdlinger et al. | |
| 2016/0237858 A1 | 8/2016 | Bergins et al. | |

FOREIGN PATENT DOCUMENTS

| | | |
|---|---|---|
| CN | 101760248 A | 6/2010 |
| CN | 102787993 A | 11/2012 |
| DE | 102006034712 A1 | 1/2008 |
| DE | 102009018126 A1 | 10/2010 |
| DE | 102011013922 A1 | 9/2012 |
| EP | 2532729 A2 | 12/2012 |
| EP | 2543743 A1 | 1/2013 |
| FR | 2939450 A1 | 6/2010 |
| FR | 2977089 A1 | 12/2012 |
| JP | 2013-092065 | 5/2013 |
| WO | WO 2000/016425 | 3/2000 |
| WO | WO 2010/069622 | 6/2010 |
| WO | WO 2011/108546 A1 | 9/2011 |
| WO | WO 2013/029701 | 3/2013 |
| WO | WO 2015/010895 | 1/2015 |

OTHER PUBLICATIONS

Japanese Office Action dated Jan. 31, 2017 for foreign Application No. 2016-524796.
Japanese Office Action dated Apr. 4, 2017 for corresponding Application No. 2016-524797.
Ichikawa et al., "New Technologies for Separation, Fixation and Conversion of Carbon Dioxide to Mitigate Global Warming", Hitachi Review. (1993) 42(6):255-260.
International Search Report and Written Opinion dated Oct. 27, 2014, for International Application No. PCT/EP2014/064625 filed Jul. 8, 2014.
International Search Report and Written Opinion dated Oct. 27, 2014, for International Application No. PCT/EP2014/064627 filed Jul. 8, 2014.
Chinese Office Action and Search Report dated Dec. 28, 2016 for foreign Application No. 201480049578.4.

* cited by examiner

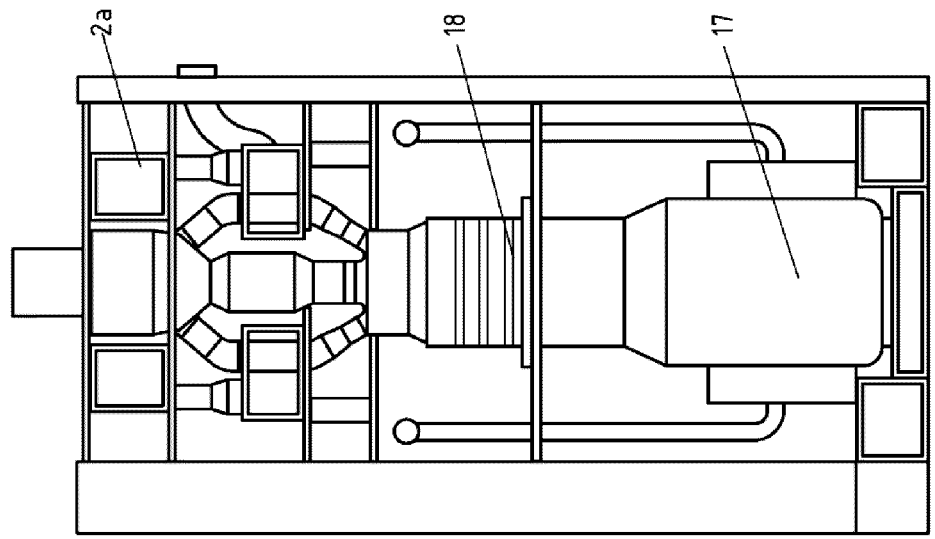
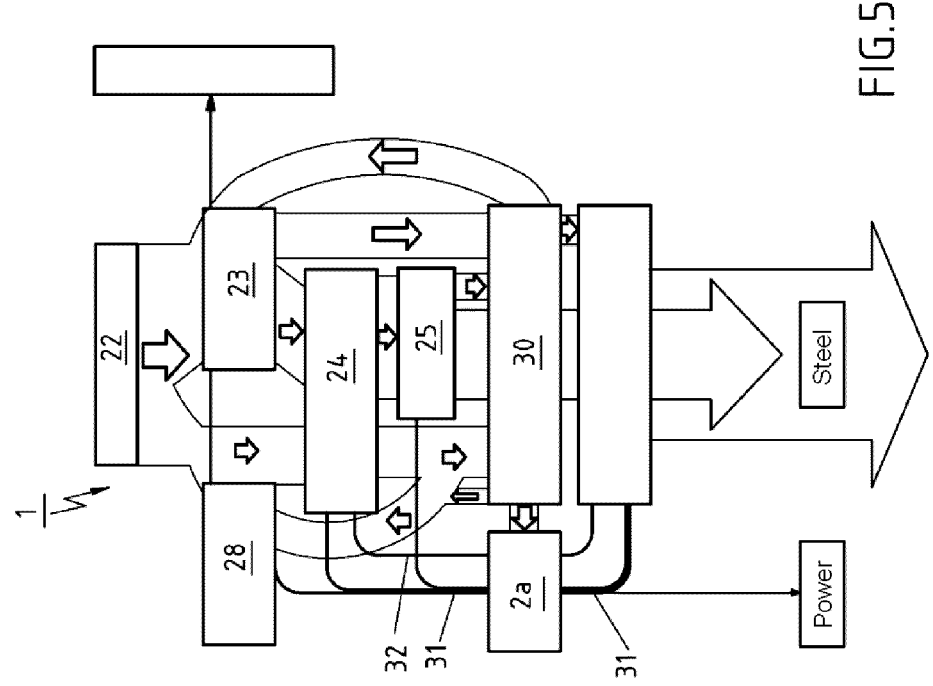
FIG.5

METHANATION METHOD AND POWER PLANT COMPRISING $CO_2$ METHANATION OF POWER PLANT FLUE GAS

RELATED APPLICATIONS

This application is the U.S. National Phase of Application No. PCT/EP2014/064625 entitled "METHANATION METHOD AND POWER PLANT COMPRISING $CO_2$ METHANATION OF POWER PLANT FLUE GAS" filed Jul. 8, 2014, which designated the United States, and which claims the benefit of German Application No. 10 2013 107 259.3 filed Jul. 9, 2013; German Application No. 10 2014 103 311.6 filed Mar. 12, 2014; and German Application No. 10 2014 105 067.3 filed Apr. 9, 2014.

The invention is directed to a methanation process comprising the conversion of $CO_2$, more particularly $CO_2$ gas, originating, more particularly diverted or obtained, from a power station flue gas of a power station fired with a carbonaceous fuel, more particularly of a power station fired with a carbonaceous gas, with attached water/steam circuit, into methane ($CH_4$) in a methanation plant.

The invention is further directed to the use of a methanation process of this kind.

Lastly the invention is also directed to a power station or a combustion plant with attached water/steam circuit that comprises a combustion chamber of a steam generator, said chamber being fired with a carbonaceous fuel, more particularly with a carbonaceous gas, and said station or plant being designed more particularly as an integral constituent of an industrial plant, more particularly of a smelting works or of a chemical works, where the flue gas line of the combustion chamber of the steam generator of the power station or of the combustion plant stands in a line connection, said line connection carrying flue gas, more particularly power station flue gas, and/or $CO_2$, more particularly $CO_2$ gas, obtained therefrom, with a methanation plant or a methanator that reacts said gas to form methane ($CH_4$).

It is known that $CO_2$ is one of the greenhouse gases considered to be one of the causes of the warming of the Earth's climate. Consequently there are numerous environmental-policy and technological efforts to reduce the emission of $CO_2$. One of these approaches is concerned with the storage of $CO_2$ through the conversion of $CO_2$ into methane gas, and is described in, for example, the article "New technologies for separation, fixation and conversion of carbon dioxide to mitigate global warming" (Hitachi, Vol. 42 (1993), No. 6, pages 255-260). In this case, the $CO_2$ arising during the combustion of fossil fuels is separated from the flue gas and supplied to a methanation in which synthetic natural gas (methane) is formed. The methanation is a chemical reaction in which carbon monoxide (CO) or carbon dioxide ($CO_2$) is converted into methane ($CH_4$). The reaction of carbon dioxide to form methane is also termed the Sabatier process, and was discovered in 1902 by Paul Sabatier and J. B. Sendersens. In the course of this reaction, carbon monoxide or carbon dioxide reacts at temperatures of 300-700° C. with hydrogen to form methane and water. The reaction is exothermic, but has to be accelerated by a catalyst.

In connection with the generation of renewable energy by means of wind power or solar energy, moreover, the problem arises that frequently more power is fed into the grid than is being demanded at the time. This leads to a quantity of what is called "excess power", which must be consumed or stored in order to ensure stability of the grid. Additionally, independently of the feeding into a grid of power generated from a regenerative energy source, the fundamental problem arises of being able to store generated power, where appropriate, in order to be able to utilize this energy at any desired point in time.

One approach which has proven advantageous in this context is that referred to as "power to gas", whereby the energy is converted chemically by means of methanation and stored as methane ($CH_4$). In this case, the hydrogen needed for the formation of the methane is generated in particular by means of an electrolysis, which obtains the required power from a renewable energy source, such as wind turbines or solar cells. Appropriate sources of $CO_2$ or CO include worked-up flue gas streams from power stations or industrial plants in which carbonaceous fuel or carbonaceous feedstocks are converted into a $CO_2$— or CO-containing gas atmosphere. The "power to gas" approach represents a sensible method for the relatively long-term storage of energy and avoidance of direct $CO_2$ emissions into the atmosphere, since the methane ($CH_4$) product arising in the methanation can be stored as synthetically generated natural gas in existing infrastructure installations (pipelines, natural gas stores) on a long-term basis, for months. Hydrogen preparation can take place by electrolysis. Alternatively, the hydrogen may originate from other, alternative sources. The $CO_2$ may originate from its separation from a $CO_2$-rich stream, an example being the flue gas stream of a power station. The $H_2$ and $CO_2$ components obtained in these ways are converted by synthesis into $H_2O$ and $CH_4$ in a methanation plant or a methanator.

In large-scale industrial plants, such as smelting works or chemical works, a further factor is that the political and resultant statutory boundary conditions make it appear rational for $CO_2$-containing exhaust gas streams and exhaust gases arising as part of the production operations to be supplied, where appropriate, likewise to an economically and energetically advantageous use. It is known, accordingly, in smelting works to use coproduct gas power stations which use process gases/coproduct gases arising, in the context of steel production, in the coking plant, the blast furnaces and/or in the steel works for the purpose of power generation and heat recovery.

A process of the generic kind is known from the article "New technologies for separation, fixation and conversion of carbon dioxide to mitigate global warming" (Hitachi, Vol. 42 (1993), No. 6, pages 255-260).

It is an object of the invention to provide a solution which allows a power station and a methanation plant to be coupled with one another in an energetically favorable way.

A further aspect is intended to permit a (more) energetically favorable incorporation of a power station, more particularly of a coproduct gas power station that is an integral and/or integrated constituent of an industrial plant, into the production operation or operations which take place within the industrial plant and, preferably, to allow an improvement in the overall degree of energy efficiency of the industrial plant. A further aspect underlying the invention is that of integrating the methanation of $CO_2$ in an energetically and materially favorable way into an industrial plant, more particularly a steel works or a chemical works, that has at least one power station, more particularly a coproduct gas power station.

The above object is achieved in accordance with the invention by a methanation process as claimed in claim 1, by a use as claimed in claim 16, and by a power station or a combustion plant as claimed in claim 18.

Advantageous and/or judicious refinements of the invention are subjects of the respective dependent claims.

In the case of a methanation process of the type designated in more detail at the outset, the object is achieved in accordance with the invention in that the heat energy arising as waste heat in the conversion of $CO_2$ to methane ($CH_4$) in the methanation plant is coupled out at least partly into at least one materials stream and/or heat energy stream and this stream is supplied at least partly to at least one medium flowing into the combustion chamber of a steam generator of the power station on the burner side and/or to the water/steam circuit of the power station and/or to a $CO_2$ exhaust gas treatment or $CO_2$ workup, more particularly power station flue gas treatment plant, which is connected upstream, in terms of process engineering, of the methanation plant, and/or to one or more operating stages of an attached industrial plant.

The above object is also achieved in accordance with the invention through the use of a methanation process as claimed in any of claims 1-15 for the storage of excess electrical energy, more particularly power and/or excess power, generated by means of a power station fired with a carbonaceous fuel, and/or present in a public grid, in the form of methane ($CH_4$) generated in the methanation plant, and utilization of the heat energy arising in the methanation plant.

In the case of a power station or a combustion plant of the type designated in more detail at the outset, finally, this object is achieved in accordance with the invention in that the methanation plant or the methanator stands in at least one heat energy-carrying line connection, said connection at least partly coupling out the waste heat arising in the methanation of the flue gas or power station flue gas or $CO_2$ gas, with at least one medium flowing into the combustion chamber of the steam generator of the power station on the burner side, and/or with the water/steam circuit of the power station and/or with a $CO_2$ exhaust gas treatment or $CO_2$ workup, more particularly power station flue gas treatment plant, connected, in terms of process engineering, upstream of the methanation plant, and/or to one or more production-engineering or process-engineering units of the industrial plant.

In accordance with the invention, therefore, a methanation plant or a methanator and also a power station are coupled with one another in an energetically advantageous way in that the waste heat or heat arising on account of the exothermic methanation reaction in the methanation plant or the methanator is utilized as heat energy and, coupled out into a materials stream and/or heat energy stream, is supplied to one or more units of the power station with attached water/steam circuit. This supplying always also embraces the coupling out of the heat energy. More particularly, the coupled-out heat energy is supplied at least partly to a medium flowing into the combustion chamber of a steam generator of the power station on the burner side, said medium being, for example, the combustion oxygen or the air, and/or to the water/steam circuit of the power station and/or to a $CO_2$ exhaust gas treatment or $CO_2$ workup, more particularly a power station flue gas treatment plant, which is connected, in process engineering terms, upstream of the methanation plant or the methanator.

In those cases where the power station is attached to an industrial plant or is an integral constituent of such an industrial plant, the materials stream and/or heat energy stream which transports the coupled-out heat energy can be supplied at one or more operating stages of the attached industrial plant.

Since, in a case of this kind, the materials streams and energy streams of the power station are then preferably integrated into the industrial plant, it is possible for at least one energetically utilizable fuel, arising as byproduct or waste product in the industrial plant, to be burnt in the power station to form $CO_2$-containing flue gas, with the flue gas then being at least partly converted into methane, $CH_4$, and the waste heat arising in the exothermic reaction of the methanation being supplied at least partly again to the power station or to the industrial plant. This enhances not only the energy balance of the power station but also that of the industrial plant. Since the materials streams and energy streams of the power station are integrated into the industrial plant, the excess energies which emerge in the form of waste heat in the separation/accumulation of $CO_2$ and in the methanation, and which arise during the exothermic chemical reactions, can be supplied directly to the power station and/or to the industrial plant again, and are therefore able to contribute to an improvement in the overall energetic balance of the power station and hence of the industrial plant.

In a refinement, therefore, the invention is distinguished in that the power station, more particularly the combustion chamber of the steam generator, is supplied with a coproduct gas comprising one or more gaseous byproducts or waste products of an industrial plant, more particularly of a chemical works or of a smelting works, preferably in the form of a gas mixture, more particularly with a coproduct gas comprising blast furnace gas and/or coking plant gas, as carbonaceous materials stream and fuel.

Moreover, in a refinement, therefore, the invention is distinguished in that the power station is designed as an integral constituent of the attached industrial plant and is integrated into at least a part of the materials streams and/or energy streams of the industrial plant, and at least a part of at least one, more particularly gaseous, carbonaceous material or materials stream obtained as byproduct or waste product in the course of a production operation in the industrial plant is supplied as carbonaceous fuel to the combustion chamber of the steam generator of the power station.

In this case it is particularly appropriate when at least a part of the power station flue gas arising in the combustion of the carbonaceous fuel, more particularly of the carbonaceous material or materials stream, in the combustion chamber of the steam generator of the power station, or of the $CO_2$ gas present in the power station flue gas, is supplied to the methanation plant, preferably after the $CO_2$ exhaust gas treatment or $CO_2$ workup of the power station flue gas, more particularly in the power station flue gas treatment plant, as likewise envisaged by the invention.

Since the $CO_2$ exhaust gas treatment or $CO_2$ workup, more particularly power station flue gas treatment plant, envisaged optionally for the purpose of obtaining a $CO_2$-rich materials stream customarily requires a supply of heat energy, it is an advantage, according to a further refinement of the invention, that at least a part of the heat demand required for the $CO_2$ separation or $CO_2$ workup is supplied to the $CO_2$ separation or the $CO_2$ exhaust gas workup, more particularly to the power station flue gas treatment plant, in the form of a materials stream and/or heat energy stream fed from the waste heat of the methanation plant.

One particularly advantageous embodiment of a $CO_2$ exhaust gas treatment is represented by post-combustion capture operations or post-combustion carbon capture operations. Therefore, in an advantageous refinement, the invention is further distinguished in that the $CO_2$, more particularly $CO_2$ gas, is obtained, more particularly separated, from the power station flue gas at least partly in the $CO_2$ exhaust gas treatment or the $CO_2$ workup, more particularly in the power station flue gas treatment plant, by means of a Post-Combustion (Carbon) Capture operation (PCC or PCCC operation), more particularly by means of a $CO_2$ gas scrubber with an absorbent.

Since, moreover, in PCC or PCCC operations of this kind it is possible for waste heat to be obtained here as well, the invention further provides that the heat energy arising as waste heat in the $CO_2$ exhaust gas treatment or $CO_2$ workup, more particularly power station flue gas treatment plant, connected, in terms of process engineering, upstream of the methanation plant is coupled out at least partly into a materials stream and/or energy stream and this stream is supplied at least partly to at least one medium flowing into the combustion chamber of the steam generator of the power station on the burner side and/or to the water/steam circuit of the power station and/or to the methanation plant which is connected, in terms of process engineering, downstream, and/or to one or more operating stages of the attached industrial plant.

In order to accomplish the necessary energy supply in the context of a PCC or PCCC operation, a development of the invention further envisages that at least a part of the heat demand required for the $CO_2$ separation or $CO_2$ workup is supplied to the $CO_2$ separation or $CO_2$ workup, more particularly to the power station flue gas treatment plant, in the form of tapped steam diverted from the water/steam circuit of the power station.

In order to be able to utilize the generated methane in particular for the purpose also of the storage of electrical energy, in a particularly advantageous and appropriate way, the invention is further distinguished in that the methanation plant and/or the $CO_2$ exhaust gas treatment or $CO_2$ workup, more particularly the power station flue gas treatment plant, is operated, in times of excess power in the public power grid, at least partly or temporarily with this power and/or the methanation plant and/or the $CO_2$ exhaust gas treatment or $CO_2$ workup, more particularly the power station flue gas treatment plant, is supplied with power generated by means of a generator attached to the water/steam circuit of the power station.

Since hydrogen is required for the methanation of the $CO_2$, it is appropriate to provide for this purpose an electrolysis or electrolysis unit, which in particular is also integrated into the same industrial plant as the power station, and which, moreover, is operated with excess power and/or with power generated by the power station. In a development, accordingly, the invention provides both that the hydrogen supplied to the methanation plant is generated at least partly or temporarily by means of an electrolysis, more particularly an electrolysis integrated into the industrial plant, and that the electrolysis, in times of excess power in the public power grid, is operated at least partly or temporarily with this power and/or the electrolysis is supplied with power generated by means of a generator attached to the water/steam circuit of the power station.

In the case of a power station integrated into an industrial plant, as for example into a smelting works or a chemical works, however, it is also possible that the hydrogen required in the methanation plant for the methanation of the $CO_2$ is obtained in the region of the industrial plant at least partly or temporarily from one or more coproduct gases, more particularly by means of pressure swing absorption or membrane separation, as likewise envisaged by the invention.

It is advantageous, furthermore, that oxygen arising as a coproduct in the electrolysis is supplied as materials stream and/or energy stream to one or more operating stages of the industrial plant and/or to the power station as process gas, more particularly to the combustion chamber of the steam generator as oxidant, and this likewise distinguishes the invention.

Since it may be rational and appropriate, depending on the type of power station, to recirculate at least a part of the flue gas into the combustion chamber of the steam generator of the power station, provision is made, according to a further refinement of the invention, that the power station, more particularly the combustion chamber of the steam generator, is supplied with recirculated power station flue gas as materials stream and/or energy stream.

The methane generated with the methanation process of the invention can then be used in a customary way; more particularly, provision may additionally be made in accordance with the invention that the methane ($CH_4$) arising in the methanation plant is wholly or partly supplied as materials stream and/or energy stream to a production operation, more particularly to a conversion operation, preferably of the industrial plant and/or is fed into a natural gas grid and/or is stored in a container.

Since the methanation process of the invention can be applied with particular advantage as an integral constituent of an industrial plant, more particularly of a smelting works or of a chemical works, the refinement of the use is distinguished in that it embraces the use of the methanation process in an industrial plant, more particularly a smelting works or a chemical works that comprises the power station, more particularly a coproduct gas power station, which has an attached $CO_2$-separating power station flue gas treatment plant, more particularly in the form of a $CO_2$ gas scrubber by means of an absorbent (PC(C)C=Post-Combustion (Carbon) Capture), for the power station flue gas and which has, connected downstream thereof, a methanation plant or methanator wholly or partly processing the $CO_2$ stream separated in the power station flue gas treatment plant, the methanation plant or the methanator being supplied with hydrogen originating from a hydrogen source, more particularly obtained by means of an electrolysis, for the reaction, more particularly catalytic reaction, of the $CO_2$, more particularly $CO_2$ gas (8), supplied from the power station flue gas treatment plant, under methane ($CH_4$)-generating conditions, where power generated by a generator, which is driven by a turbo set or turbine set disposed in the water/steam circuit of the power station, and/or power originating as excess power from the public grid and supplied to the methanation plant and/or to the flue gas treatment plant and/or to the electrolysis is stored in the methane ($CH_4$) of the methanation plant or the methanator.

In a likewise advantageous way, the power station is distinguished first of all in that the line connection carrying power station flue gas and/or $CO_2$ gas obtained therefrom comprises a $CO_2$ exhaust gas treatment or $CO_2$ workup, more particularly power station flue gas treatment plant, which is connected, in process engineering terms, upstream of the methanation plant or the methanator, and which stands, in the direction of gas flow, on the input side in flue gas-, more particularly power station flue gas-, supplying line connection with the combustion chamber of the steam generator and, on the output side, in $CO_2$ gas-discharging line connection with the methanation plant or the methanator, and which stands in a heat energy-carrying line connection, said line connection coupling out the waste heat arising in the $CO_2$ exhaust gas treatment or $CO_2$ workup, more particularly in the power station flue gas treatment, with at least one medium flowing on the burner side to the combustion chamber of the steam generator, and/or with the water/steam circuit of the power station and/or of the methanation plant connected downstream in terms of process engineering, and/or with one or more production-engineering or process-engineering units of the industrial plant.

In this context it is further of advantage if the $CO_2$-separating CO2 exhaust gas treatment plant or CO2 workup, more particularly power station flue gas treatment plant, is designed as a $CO_2$ gas scrubber by means of an absorbent (PC(C)C=Post-Combustion (Carbon) Capture), as likewise envisaged by the invention.

For reasons of energy engineering it is additionally of advantage if a power station flue gas treatment plant of this kind is supplied with the required heat energy from the water/steam circuit of the power station. In a refinement, therefore, the invention further provides that the $CO_2$ exhaust gas treatment or $CO_2$ workup, more particularly power station flue gas treatment plant, stands in media-carrying line connection with the water/steam circuit, by means of which it can be supplied with tapped steam.

An appropriate hydrogen source for the methanation is an electrolysis. The invention is therefore further distinguished in that the methanation plant or the methanator stands in media-carrying line connection with a hydrogen source, more particularly an electrolysis.

For the purpose of supplying the methanation and other plant parts of the power station with electrical energy, the electrical power which can be generated with the power station is usefully appropriate. The invention therefore further envisages that the power station or the combustion plant comprises a generator, which is attached to its water/steam circuit and is driven, in particular, by a turbo set disposed in the water/steam circuit, said generator standing in power-conducting line connection with the methanation plant or the methanator and/or with the $CO_2$ exhaust gas treatment or the $CO_2$ workup, more particularly the power station flue gas treatment plant, and/or with the electrolysis.

In this context, however, especially from the standpoint of the possibility of storage for electrical power generated from regenerative energy, it is advantageous if the methanation plant or the methanator and/or the $CO_2$ exhaust gas treatment or the $CO_2$ workup, more particularly the power station flue gas treatment plant, and/or the electrolysis stands or stand in an excess power-supplying, power-conducting line connection with an attached public power grid. So-called excess power is nowadays frequently available in the public power grid by means of power generated by plants that utilize regenerative energies, since frequently the amount of power generated by means of regenerative power generation, as for example by wind turbines or solar plants, is larger than, rather than coinciding with, the amount of power taken from the public power grid.

In the context of the power station of the invention it is a particular advantage, moreover, for the power station to be integrated into an industrial plant, since the waste products or byproducts otherwise arising in the industrial plant can then find use advantageously. In a development, therefore, the invention is also distinguished in that the power station or the combustion plant has a line which stands in media-carrying line connection with one or more production-engineering or process-engineering units of an industrial plant and which supplies a carbonaceous fuel to the combustion chamber of the steam generator of the power station, and by means of which the combustion chamber of the steam generator can be supplied with a carbonaceous, more particularly gaseous, material or materials stream, which comprises one or more, more particularly gaseous, byproducts or waste products of the production-engineering or process-engineering units of the industrial plant, preferably in the form of a gas mixture, as carbonaceous fuel, more particularly in the form of a coproduct gas, preferably of a coproduct gas comprising blast furnace gas and/or coking plant gas.

In a very particular way, the power station of the invention is suitable for refinement as a coproduct gas power station, and so the invention is distinguished in that the power station is a coproduct gas power station, more particularly a blast furnace gas power station or a coking plant gas power station, which is integrated into an industrial plant, more particularly a smelting works or a chemical works, and the line connection which carries the power station flue gas or $CO_2$ gas obtained therefrom supplies the methanation plant and/or the $CO_2$ exhaust gas treatment or $CO_2$ workup, more particularly power station flue gas treatment plant, with at least a part of the power station flue gas arising in the combustion of the carbonaceous fuel in the combustion chamber of the steam generator.

Lastly, the power station or the combustion plant is also further distinguished in that it is configured for implementing a process as claimed in any of claims 1-15 and/or for the use as claimed in claim 16 or 17.

Figure 2:
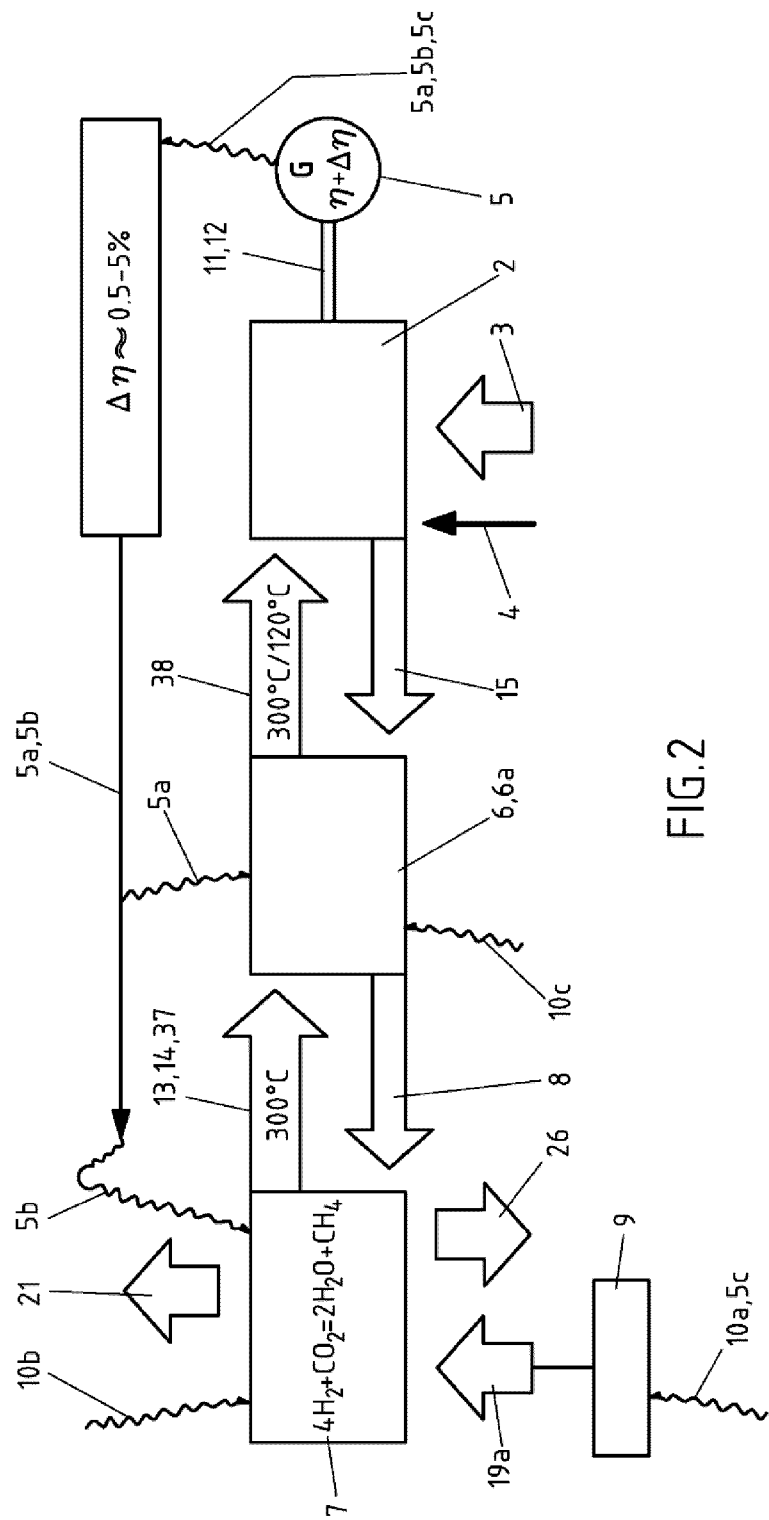
Figure 3:
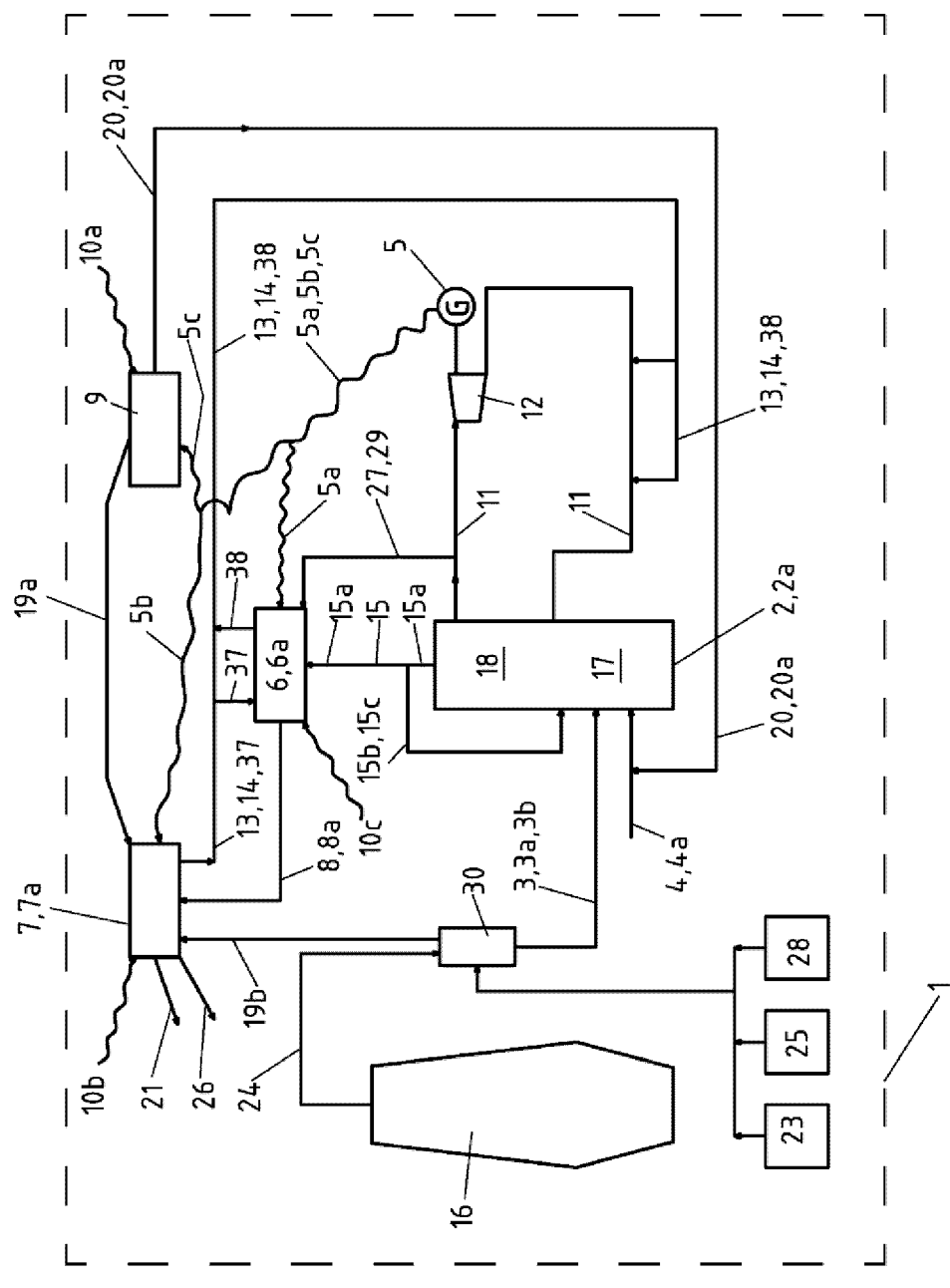
Figure 4:
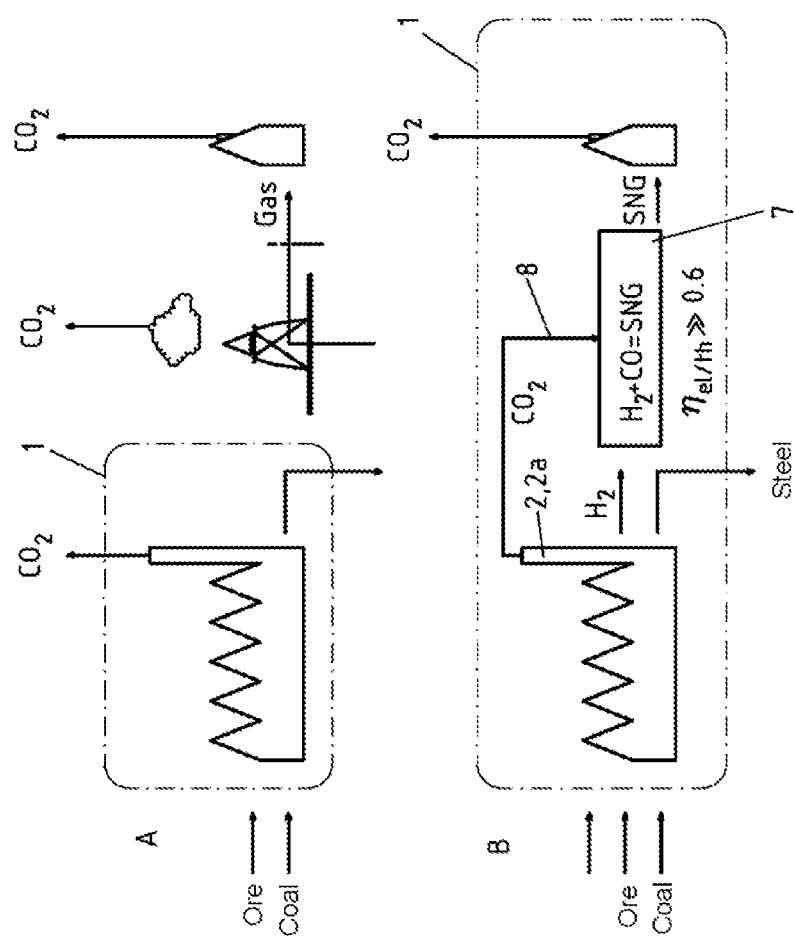
Figure 6:
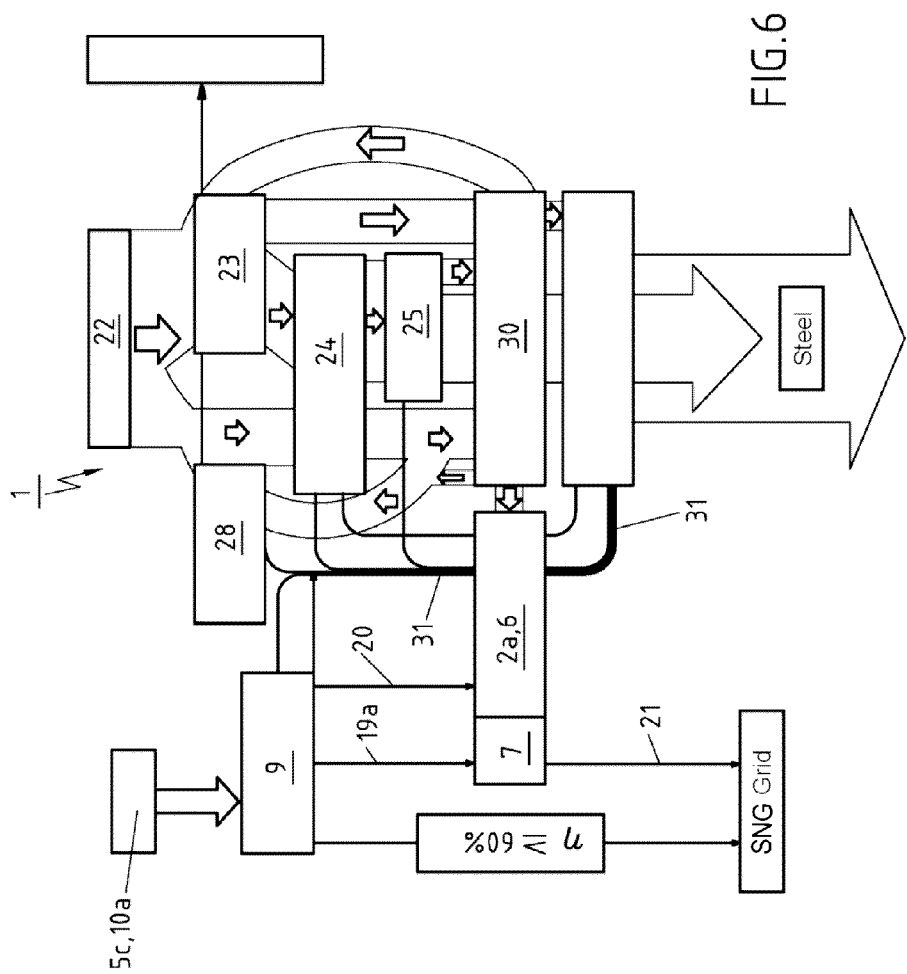
Figure 7:
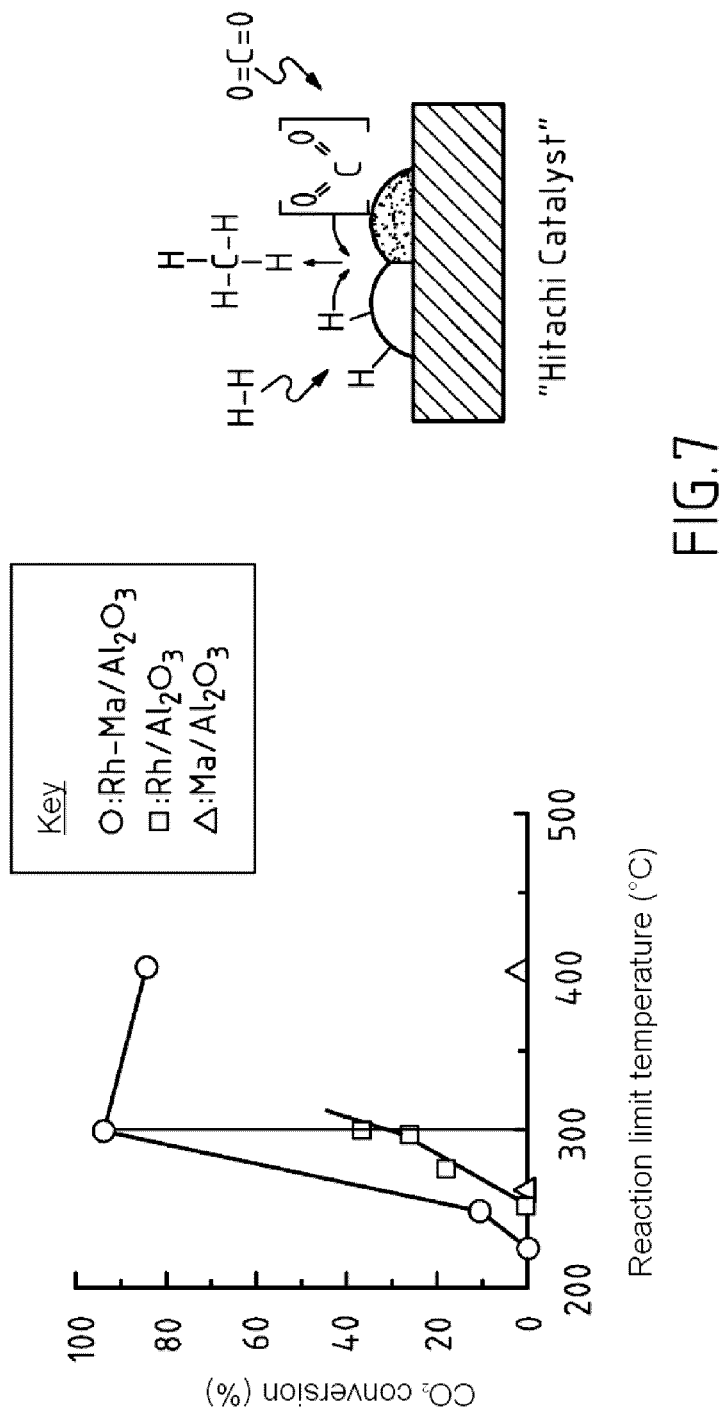
Figure 8:
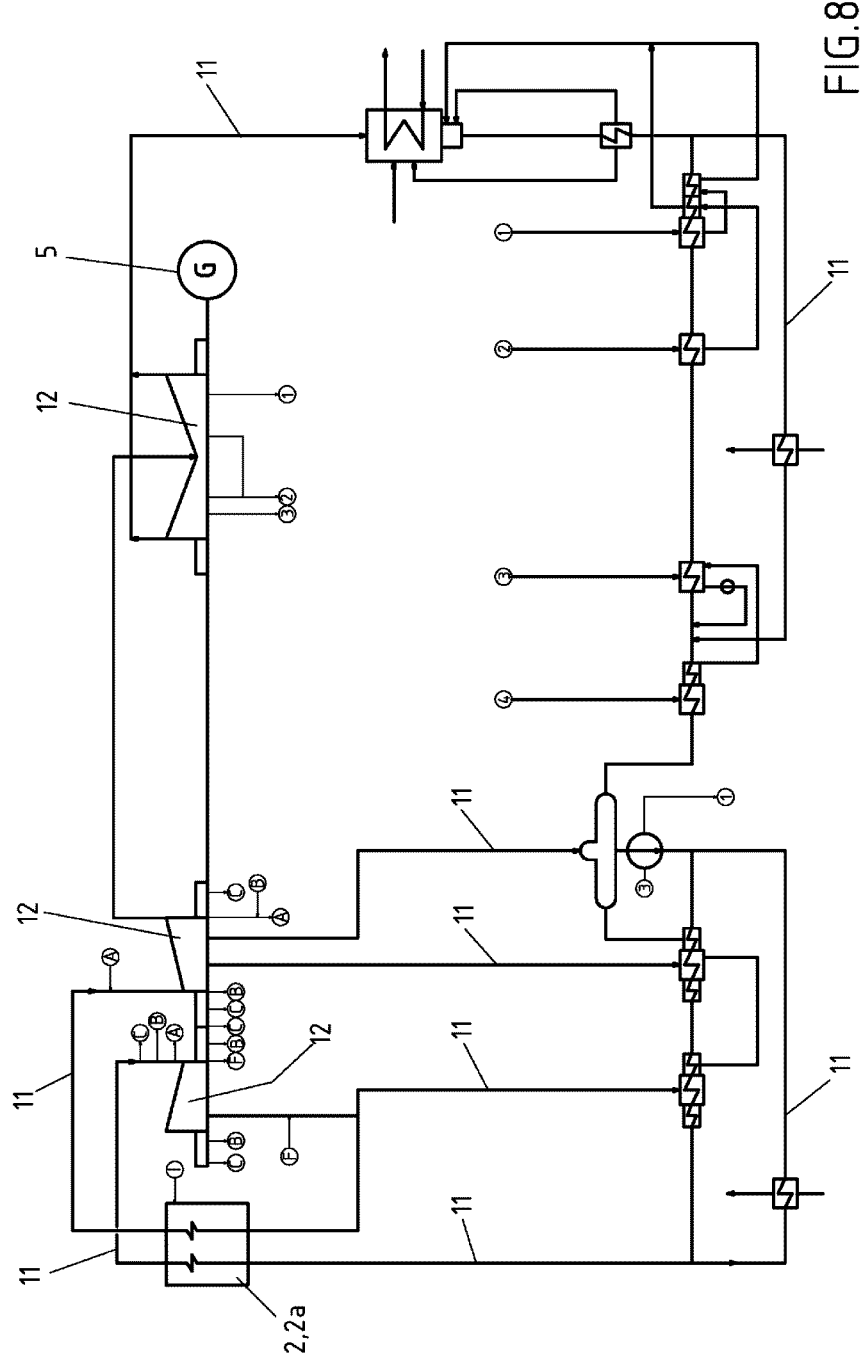
Figure 9:
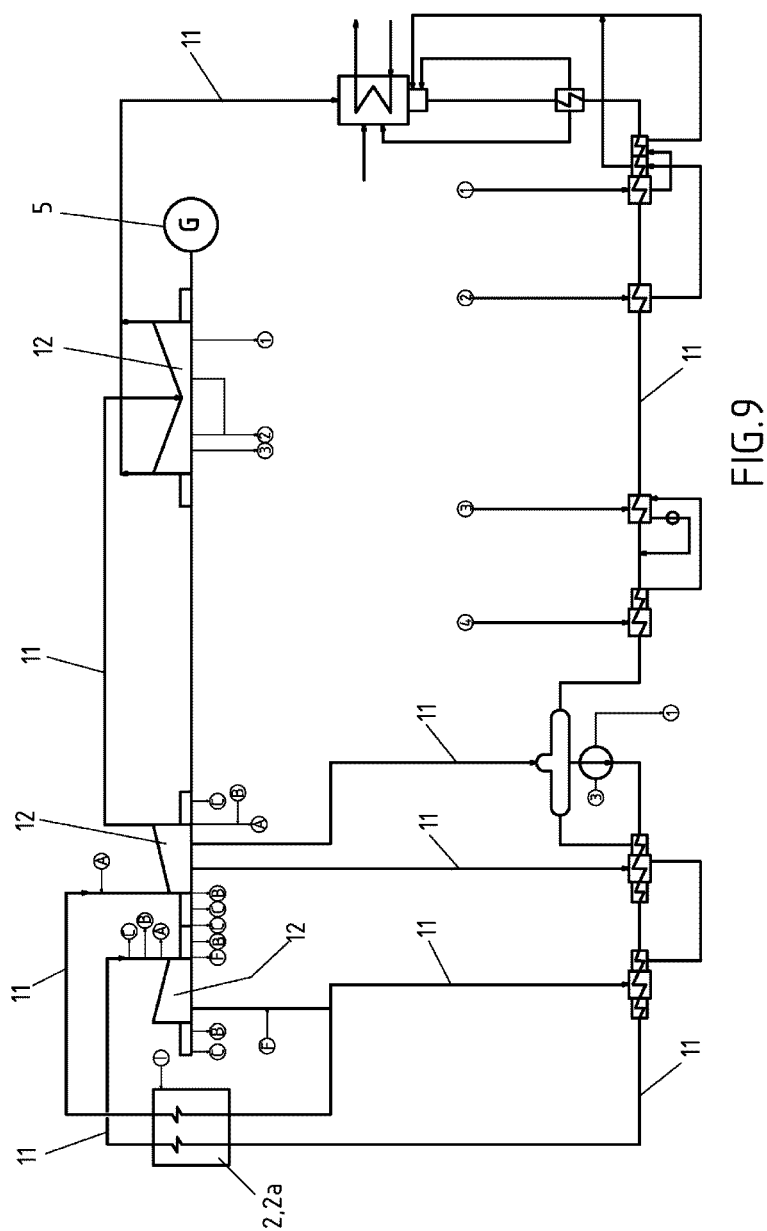

The invention is elucidated in more detail below by way of example with reference to a drawing. In said drawing, FIG. 1 shows in schematic representation a power station of the invention, FIG. 2 shows in schematic representation a further exemplary embodiment of a power station of the invention, FIG. 3 shows in schematic representation a coproduct gas power station of the invention, integrated into a smelting works, FIG. 4 shows in schematic representation a comparison between a prior-art process and the process of the invention, FIG. 5 shows a schematic representation of a smelting works with a coproduct gas power station without attached methanation plant, FIG. 6 shows a schematic representation of a smelting works with a coproduct gas power station with methanation plant attached in accordance with the invention, FIG. 7 shows a schematic representation of the catalyst, FIG. 8 shows a schematic representation of a first exemplary embodiment of a water/steam circuit of a coproduct gas power station of the invention, and FIG. 9 shows a schematic representation of a second exemplary embodiment of a water/steam circuit of a coproduct gas power station of the invention.

FIG. 1 shows in schematic representation an operationally integrated "power to gas" application of a methanation process of the invention and of a power station 2 of the invention. The power station 2 comprises a steam generator 18 with combustion chamber 17 and attached water/steam circuit 11, disposed in which is a turbo set or turbine set 12 with attached generator 5. On the flue gas side, a $CO_2$ exhaust gas treatment in the form of a power station flue gas treatment plant 6a is attached to the power station 2 or the combustion plant. The combustion chamber 17 and the steam generator 18 are connected via a line 15a to the power station flue gas treatment plant 6a, and flue gas 15 is supplied to the power station flue gas treatment plant 6a by means of the flue gas line 15a. The flue gas 15 arises in the combustion chamber 17 of the steam generator 18 as a result of combustion of a carbonaceous materials stream 3a as fuel 3, with an oxygen-containing medium 4 being supplied as oxidant.

In the power station flue gas treatment plant 6a, which is designed as a PCC (Post-Combustion Capture) plant, the flue gas is worked up into a $CO_2$ gas stream 8, which has a high $CO_2$ fraction, and is passed in a line connection 8a to a methanation plant 7. The power station flue gas treatment plant 6a is a customary $CO_2$ gas scrubber with an absorbent, wherein the $CO_2$ is removed from the flue gas 15 by means of the absorbent and subsequently separation from the $CO_2$ takes place. Such processes are customary in the prior art, and so are not addressed in detail here.

In the methanation plant 7, in a likewise customary process which is known from the prior art, the carbon dioxide ($CO_2$) supplied in the $CO_2$ stream 8 is reacted, by means of hydrogen ($H_2$) obtained with an electrolysis 9 and supplied, 19a, to form methane ($CH_4$), which is taken off from the methanation plant 7 as materials stream and energy stream 21. Similarly, water formed is guided off from the methanation plant 7 as materials stream and energy stream 26.

The heat energy arising as waste heat in the $CO_2$ conversion of the $CO_2$ gas 8 into methane 21 in the methanation plant 7 is coupled out at one or more locations 33, 34 at least partly into a materials stream and/or heat energy stream 13, 14. The two energy streams 13 and 14 are supplied to the water/steam circuit 11 of the power station 2 and their heat energy content is coupled by means of suitable devices 35, 36 into the water/steam circuit 11. Examples of devices for this purpose are heat exchangers. Depending on the heat energy content of the materials streams and/or heat energy streams 13, 14, the coupling takes place into a high-energy or low-energy region of the water/steam circuit 11. For this purpose, the materials streams and/or heat energy streams 13 and 14 coupled out from the methanation plant stand in fluid-conducting connection, via line connections 13a and 14a, with the water/steam circuit 11 of the power station 2.

FIG. 2 shows a further exemplary embodiment of an operationally integrated "power to gas" application, which relative to the embodiment according to FIG. 1 is represented with yet further schematicization, and which differs essentially in the supplying of electrical power 5a, 5b, 5c and/or of excess power 10a, 10b, 10c to the electrolysis 9, to the methanation plant 7 and/or to the power station flue gas treatment plant 6a and also in the supplying of a materials stream and/or heat energy stream 37 from the methanation plant 7 to the power station flue gas treatment plant 6a, and in a materials stream and/or heat energy stream 38 which is coupled out from the power station flue gas treatment plant 6a and is recycled for the purpose of heat reintegration into the power station 2, from the exemplary embodiment according to FIG. 1.

FIG. 2 shows a power station 2 whose flue gas 15 is supplied to a power station flue gas treatment plant 6a, where it is worked up into a $CO_2$ stream 8, which is supplied to the methanation plant 7. In the methanation plant 7, hydrogen 19a obtained by an electrolysis 9 is converted with the inflowing $CO_2$ 8 to form a materials stream and energy stream 21 composed of methane and a materials stream and energy stream 26 composed of water, which leave the methanation plant 7. Of the materials streams and/or heat energy streams 13, 14, and 37 leaving the methanation plant 7, at least a part, in this case the heat energy stream 37, is supplied to the power station flue gas treatment plant 6a. There, the heat energy contained in the materials stream and/or heat energy stream 37 is coupled out for the purpose of implementing the $CO_2$ separation operation in the power station flue gas treatment plant 6a. The waste heat arising in the $CO_2$ separation is coupled out in turn into a materials stream and/or heat energy stream 38, which is supplied to the power station 2 where it is coupled by reintegration into the water/steam circuit 11, for example.

Furthermore, in the case of the embodiment according to FIG. 2, power is generated with the generator 5 attached to the water/steam circuit. This power is supplied as operating power 5a to the power station flue gas treatment plant 6a and as operating power 5b to the methanation plant 7. As a result of this power supply, an improvement in the efficiency of the power station of 0.5-5% points can be achieved. Another part of the power generated by means of the generator 5 can be supplied as operating power 5c to the electrolysis which, however, is preferably operated with excess power 10a when such power is in excess in the public grid. The methanation plant 7 can also be operated with excess power 10b, and the power station flue gas treatment plant 6a with excess power 10c.

FIG. 3 shows, in a schematic overview representation, a power station 2 which is integrated into an industrial plant formed by a smelting works 1 and which is designed as a coproduct gas power station 2a. The combustion chamber 17 of the steam generator 18 is supplied with blast furnace gas 30, derived from a blast furnace 16, as carbonaceous fuel 3 via a line 3b. The coproduct gas 30 may be a gas mixture composed of a plurality of product gases of the smelting works 1. From the steam generator 18, the flue gas 15 arising in the combustion chamber 17 enters via a flue gas line 15a into a power station flue gas treatment plant 6a. A part of the power station flue gas 15 is returned to the combustion chamber 17 as recirculated flue gas 15c via a flue gas line connection 15b. In the power station flue gas treatment plant 6a, the flue gas 15 is freed from $CO_2$. The $CO_2$ gas stream 8 arising is supplied via a line connection 8a to the methanation plant 7 or the methanator 7a. Here, the $CO_2$ gas 8 is converted into methane 21 and water 26. The waste heat arising in this process is coupled out and reintegrated as materials streams and/or heat energy streams 13, 14 into the water/steam circuit 11 of the power station 2, by coupling-out therein. Here, however, the materials stream and/or heat energy stream 37 can also be supplied to the power station flue gas treatment plant 6a. Any waste heat arising in the power station flue gas treatment plant 6a can be coupled out as materials stream and/or heat energy stream 38 and supplied likewise to the water/steam circuit 11. The materials streams and/or heat energy streams 13, 14, 37, and 38 are carried in respectively assigned line connections 13a, 14a, 37a, and 38a. The heat energy needed for the operation of the power station flue gas treatment plant 6a can be supplied to said plant by means of tapped steam 27 tapped from the water/steam circuit 11, via a line connection 29.

The hydrogen 19a needed in the methanation plant 7 can be generated by means of an electrolysis 9 and supplied to the methanation plant 7 via a hydrogen-carrying line connection 19. Another possibility, however, is to supply hydrogen 19b obtained from the coproduct gas 30 to the methanation plant 7. The oxygen 20 arising in the electrolysis 9 or electrolysis unit can be supplied to the combustion chamber 17 as process gas 20a or as oxygen-containing medium 4, more particularly as pure oxygen 4a. The power required respectively for the electrolysis 9 and/or for the implementation of the methanation in the methanation plant 7 and/or the power required respectively for the $CO_2$ separation in the $CO_2$ exhaust gas treatment 6, more particularly the power station flue gas treatment plant 6a, is advantageously and usefully supplied to these plants in the form, in particular, of excess power 10a, 10b, 10c, if in the attached public grid there is an excess supply of electrical power, in other words an excess power. In order to ensure the operation of these plants, however, it is possible, moreover, for the respectively required operating power to be generated by means of the generator 5 attached to the water/steam circuit 11 of the power station 2 and for it to be supplied as operating power or power 5a, 5b, 5c to the plant in question, as shown in FIG. 3.

FIGS. 4 and 6 show, in a schematic representation, exemplary embodiments of the invention wherein an industrial plant is realized as a smelting works 1, represented schematically as a dashed line. A constituent of the smelting works 1 is a coproduct gas power station 2a in the form of a blast furnace gas power station, in which blast furnace gas 24 originating from a blast furnace 16 is burnt as coproduct gas 30 with supply of an oxygen-containing medium 4. In this case, power station flue gas 15c recycled from the exhaust gas space of the combustion chamber 17 of a steam generator 18 of the power station 2a, or a $CO_2$-enriched gas stream, may also be passed into the coproduct gas power station 2a and may additionally find use in the combustion of the coproduct gas 30 or in the conversion of furnace gas constituents.

The power station flue gas 15 arising during the combustion of the coproduct gas 30 and emerging from the coproduct gas power station 2a is intended in particular to have a $CO_2$ fraction of at least about 30 wt % or vol %, and hence it is particularly advantageous to supply the coproduct gas power station 2a, for the purpose of combustion of the coproduct gas 30, with a pure oxygen stream 4a or with a highly oxygen-enriched gas stream which has a higher oxygen fraction than does air.

As represented in FIGS. 3 and also 8 and 9, a steam generator 18 with a water/steam circuit 11 with integrated turbine set 12 is attached in a customary way to the fire compartment or the combustion chamber 17 of the coproduct gas power station 2a, into which the coproduct gas 30 and the oxygen-containing medium 4 are introduced for combustion. The turbo set 12 communicates in a customary way with a generator 5 for power generation. By means of the coproduct gas power station 2 with attached generator 5, power can be generated with an efficiency η. This efficiency η alters, i.e. improves, by an amount Δη of 0.5-5% points if at least a part of the energy generated with the generator 5 in the form of electrical power 5a, 5b, 5c is utilized in order to provide electrical energy for a $CO_2$ exhaust gas treatment 6 or power station flue gas treatment plant 6a and/or for a methanation 7 or a methanator 7a and/or for an electrolysis 9, which are shown in the operational schemes depicted in FIGS. 1 to 3, such provision of energy being as depicted schematically by means of the arrows 5a, 5b and 5c shown in jagged form in FIGS. 2 and 3.

In a downstream $CO_2$ exhaust gas treatment 6 or power station flue gas treatment plant 6a, the $CO_2$-containing power station flue gas 15 originating from the coproduct gas power station 2a is freed from the $CO_2$ by means of a $CO_2$ separation operation or a scrubbing process, and is worked up to give a virtually pure, highly $CO_2$-containing gas stream 8. The $CO_2$ exhaust gas treatment 6 involves more particularly the implementation of a Post-Combustion (Carbon) Capture operation (PCC or PCCC operation). A $CO_2$ gas scrubber or a $CO_2$ gas scrub is preferably part of the PCC or PCCC operation and hence of the $CO_2$ exhaust gas treatment 6, by means of which the power station flue gas is worked up with an absorbent, more particularly with an amine-containing absorbent, which is preferably regenerated again. The amines accumulate with the carbon dioxide and, with heat being supplied, the $CO_2$ is subsequently released in a controlled way. Amine solutions used are preferably diethanolamine (DEA), methyldiethanolamine (MDEA), and monoethanolamine.

A result of the $CO_2$ exhaust gas treatment 6 is a high-purity $CO_2$ gas stream 8, which is supplied to the methanation plant 7. In the course of the methanation, the $CO_2$ is converted by means of hydrogen ($H_2$) into methane ($CH_4$). This preferably occurs catalytically, in which case an Rh—Mn/$Al_2O_3$ catalyst, identified in FIG. 7 as "Hitachi Catalyst", has proven advantageous. The methanator 7a or the methanation plant 7 is also supplied with hydrogen ($H_2$), in which case preferably hydrogen 19a originating from an electrolysis 9 is used. In the methanation plant 7 or the methanator 7a, methane ($CH_4$) is generated by synthesis, and can then be stored in a conventional way. In order to generate the hydrogen 19a in the electrolysis 9, electrical power 10a is used, preferably so-called "excess power", arising frequently as grid overcapacity in the generation of power from regenerative energy sources. Since this power cannot be consumed in a conventional way, the methanation of $CO_2$ therefore opens up the possibility of energy storage. However, it is also possible for power 5c generated by means of the generator 5 to be used for implementing the electrolysis 9. This is especially so when the power station 2, more particularly coproduct gas power station 2a, is operated, in a resting phase, in a minimal load range, without delivering power to any attached public power grid with power production nevertheless taking place or having to take place for technical reasons.

Also used is the heat arising in the methanation and/or in the $CO_2$ exhaust gas treatment. The catalytic methanation proceeds at a temperature of about 300° C., and for this reason the waste heat of the methanation is utilized as coupled-out materials stream and/or heat energy stream 13, 14, 37 as an energy input into the $CO_2$ exhaust gas treatment 6 (heat flow 37) and/or into the coproduct gas power station 2a and/or its water/steam circuit 11 (heat flows 13, 14) and/or into one or more operating stages of the industrial plant, in the present case the smelting works 1. Another possibility is to couple out the waste heat of the $CO_2$ exhaust gas treatment 6, which is in the range between 300° C. and 120° C., as a materials stream and/or heat energy stream 38, and to utilize it in the coproduct gas power station 2a and/or its water/steam circuit 11 and/or in one or more operating stages of the industrial plant, in the present case the smelting works 1. By this means it is possible to achieve further improvement in the overall efficiency of the coproduct gas power station 2a and hence of the industrial plant, since the coproduct gas power station 2a, the $CO_2$ exhaust gas treatment 6, and the methanation are integrated into the materials streams and/or energy streams of the industrial plant, in the present case the smelting works 1. A carbonaceous materials stream 3a, in the present case blast furnace gas 30, arising as a byproduct or waste product in the industrial plant is supplied as fuel 3 to the power station 2, in the present case the coproduct gas power station 2a. A part of the power generated by the generator 5 is supplied as electrical energy 5a, 5b to the $CO_2$ exhaust gas treatment 6 downstream of the power station, and more particularly to the assigned methanation plant 7 downstream. The power station flue gas 15 of the power station 2, 2a is likewise supplied to the methanation plant 7 as a materials stream optionally worked up beforehand. From the methanation plant 7, in turn, heat energy in the form of waste heat is supplied as heat energy stream 13, 14, 37 to one or more of the operations taking place in the industrial plant and/or to the coproduct gas power station 2a, more particularly to at least one medium supplied thereto, more particularly the combustion oxygen, and/or to the $CO_2$ exhaust gas treatment 6. Heat energy in the form of waste heat is also supplied, as heat energy stream 38 originating from the $CO_2$ exhaust gas treatment 6 or power station flue gas treatment plant 6a, to the industrial plant 5 and/or to the power station 2, 2a.

Depicted in FIG. 4 in the top part A is the hitherto customary, prior-art procedure in relation to a smelting works 1 and a gas recovery. According to that procedure, iron ore and coal are smelted to form steel, with emission of $CO_2$, and natural gas is conveyed in conveying fields and also transported by a pipeline system to the end consumer. As depicted in the lower part B of FIG. 4, in accordance with the present invention, the $CO_2$ arising in a smelting works 1 is converted, in a power station 2 of the smelting works 1 that is designed as a coproduct gas power station 2a, into synthetic natural gas in the form of methane ($CH_4$), which is transported on to consumers. The resulting methane gas can then be put to energetic use by other consumers and also processed further to form methanol.

FIG. 5, in the left-hand image, shows the materials streams and energy streams which come about in the case of a coproduct gas power station 2a integrated into a smelting works 1. This system involves the introduction of coal 22, more particularly in the form of coke, and of iron ore and further materials for steel making. The product gases arising from the carbon sources in the course of the steel making in the smelting works 1, examples being coking plant gas 23, blast furnace gas 24, steelworks offgas 25, and sintering unit offgas 28, are combined as a gas mixture to form a coproduct gas 30, and passed on to the coproduct gas power station 2a. The power 31 generated by the combustion of the coproduct gases 30 in the coproduct gas power station 2a in the course of combustion in the combustion chamber 17 of a steam generator 18 with attached water/steam circuit 11 with integrated turbo set 12 and generator 5, and the heat 32 arising, are supplied again to the smelting works 1, and so as a result of this it is possible to achieve an efficiency η of approximately 42% for the coproduct gas power station 2a. If, in accordance with the invention, a power station 2, more particularly a coproduct gas power station 2a, with attached $CO_2$ exhaust gas treatment 6 and attached methanation plant 7 or attached methanator 7a is integrated into a smelting works 1 of this kind, as shown in FIG. 6, the efficiency η, for otherwise the same power station 2 or the same combustion plant, can be increased to 60%.

FIGS. 8 and 9 show different possibilities in accordance with the invention for integration of a power station 2, designed as a coproduct gas power station 2a, with attached water/steam circuit 11 and integrated turbine set 12, into a smelting works 1, the coproduct gas power station 2a being a coproduct gas power station 2a which combusts blast furnace gas 24. FIG. 8 shows a first possibility in accordance with the invention for integration of a power station 2, designed as coproduct gas power station 2a with attached water/steam circuit 11 and integrated turbine set 12, into a smelting works 1, the coproduct gas power station 2a being one which combusts blast furnace gas 24. A further integration possibility is shown in FIG. 9, and differs from that according to FIG. 8 with regard to the coupling-out of heat from the water/steam circuit 11.

Although a number of exemplary embodiments relate to a coproduct gas power station 2a, the invention can nevertheless be applied very generally to power stations 2 fired with a carbonaceous fuel 3 and to the flue gas stream 15 which forms in each case. A power station 2 is understood, consequently, to be any kind of a carbon-fired, more particularly fossil-fuel-fired, power station, more particularly large power station, i.e., a power station fired with bituminous coal or lignite coal or gas. Biomass-fired and biogas-fired power stations as well can be subsumed under the "power station" rubric, and in the case of the latter may also be not only large power stations, but also small power stations or small plants, i.e., combustion plants. A "power station flue gas" or flue gas is then the gas or the gas stream which in the case of one of the aforementioned power stations forms the exhaust gas from the combustion chamber or steam generator, respectively. Accordingly, in place of the coproduct gas power station 2a shown in FIGS. 3 and 6, any of the aforementioned types of power station may form the power station 2, which is in the operative connection described earlier on above with the methanation plant 7 or with the methanator 7a and/or with the $CO_2$ exhaust gas treatment 6, on the one hand by means of the flue gas stream 15, via the $CO_2$ exhaust gas treatment 6 and the $CO_2$-rich exhaust gas stream 8 formed therein, and also, on the other hand, by means of at least a part or one of the heat energy streams 13 and/or 14 and/or 37 and/or 38 waste heat reintegration taking place.

The waste heat coming from the methanation, more particularly from the methanation plant 7, more particularly the materials streams and/or heat energy streams 13, 14, 37, and 38, can be supplied to the water/steam circuit 11 of the power station 2, 2a at least partly to boost performance.

Likewise, the oxygen 20 arising as a coproduct in the electrolysis 9 can be used at least partly to boost the performance of the power station 2, 2a, more particularly of the power station operation or of an attached operating unit, more particularly a blast furnace 16 or a reactor. As a result of this, use is made not only of the hydrogen arising in the electrolysis, for the methanation, but also of the oxygen, thereby further increasing the overall energetic efficiency.

The invention claimed is:

1. A methanation process comprising the conversion of $CO_2$ into methane in a methanation plant, the $CO_2$ originating from a power station which is an integral and/or integrated constituent of a smelting works or chemical works, the power station fired with a carbonaceous fuel with attached water/steam circuit and from a coproduct power station flue gas of gas of the smelting works or chemical works, and wherein the power station is supplied with the coproduct gas in the form of a gas mixture, the gas mixture containing one or more gaseous byproducts of the smelting works or chemical works as carbonaceous materials stream and fuel, said process comprising coupling out a heat energy arising as waste heat in the conversion of $CO_2$ to methane in the methanation plant at least partly into at least one materials stream and/or heat energy stream wherein this stream is supplied at least partly to at least one medium flowing into a combustion chamber of a steam generator of the power station on the burner side and/or to the water/steam circuit of the power station and/or to a $CO_2$ exhaust gas treatment or $CO_2$ workup, which is connected upstream, in terms of process engineering, of the methanation plant, and/or to one or more operating stages of the smelting works or chemical works, and hydrogen obtained from the coproduct gas and generated by means of an electrolysis is supplied to the methanation plant, wherein the hydrogen required in the methanation plant for the methanation of the CO2 is obtained in the region of the smelting works or chemical works at least partly or temporarily from the one or more coproduct gases.

2. The methanation process as claimed in claim 1 wherein coupling out a heat energy arising as waste heat in the conversion of $CO_2$ to methane in the methanation plat at least partly comprises coupling out a heat energy to the $CO_2$ exhaust gas treatment or $CO_2$ workup, and wherein at least a part of the power station flue gas arising in combustion of the carbonaceous fuel in the combustion chamber of the steam generator of the power station, or of the $CO_2$ gas present in the power station flue gas, is supplied to the methanation plant, after the $CO_2$ exhaust gas treatment or $CO_2$ workup of the power station flue gas.

3. The methanation process as claimed in claim 1 wherein the $CO_2$ gas, is obtained from the power station flue gas at least partly in the $CO_2$ exhaust gas treatment or the $CO_2$ workup by utilizing a Post-Combustion (Carbon) Capture operation (PCC or PCCC operation).

4. The methanation process as claimed in claim 1 wherein the methanation plant and/or the $CO_2$ exhaust gas treatment or $CO_2$ workup is operated, in times of excess power in the public power grid, at least partly or temporarily with the excess power and/or the methanation plant and/or the $CO_2$ exhaust gas treatment or $CO_2$ workup is supplied with power generated by a generator attached to the water/steam circuit of the power station.

5. The methanation process as claimed in claim 1 wherein the hydrogen supplied to the methanation plant is generated at least partly or temporarily by electrolysis integrated into the smelting works or chemical works.

6. The methanation process as claimed in claim 5, wherein the electrolysis, in times of excess power in the public power grid, is operated at least partly or temporarily with the excess power and/or the electrolysis is supplied with power generated by a generator attached to the water/steam circuit of the power station.

7. The methanation process as claimed in claim 1 wherein the hydrogen required in the methanation plant for the methanation of the $CO_2$ is obtained in a region of the smelting works or chemical works at least partly or temporarily from the one or more coproduct gases by pressure swing absorption or membrane separation.

8. The methanation process as claimed in claim 1 wherein oxygen arising as a coproduct in the electrolysis is supplied as materials stream and/or energy stream to one or more operating stages of the smelting works or chemical works and/or to the power station as process gas.

9. The methanation process as claimed in claim 1 wherein the methane ($CH_4$) arising in the methanation plant is wholly or partly supplied as materials stream and/or energy stream to a production operation, which is a conversion operation, of the smelting works or chemical works and/or is fed into a natural gas grid and/or is stored in a container.

10. The methanation process as claimed in claim 1 further comprising storing excess electrical energy generated by said power station fired with a carbonaceous fuel, and/or present in a public grid, in the form of methane ($CH_4$) generated in the methanation plant, utilizing the heat energy arising in the methanation plant.

11. The methanation process claimed in claim 10, wherein said process is performed in the smelting works or chemical works that comprises the power station, which has an attached $CO_2$-separating power station flue gas treatment plant for the power station flue gas and which has, connected downstream thereof, a methanation plant or methanator wholly or partly processing the $CO_2$ stream separated in the power station flue gas treatment plant, the methanation plant or the methanator being supplied with the hydrogen originating from the coproduct gas and/or obtained by the electrolysis, and wherein the process is utilized for the reaction of the $CO_2$ supplied from the power station flue gas treatment plant, under methane ($CH_4$)-generating conditions, and wherein power generated by a generator, which is driven by a turbo set or turbine set disposed in the water/steam circuit of the power station and/or power originating as excess power from the public grid and supplied to the methanation plant and/or to the flue gas treatment plant and/or to the electrolysis is stored in the methane ($CH_4$) of the methanation plant or the methanator.

12. The methanation process claimed in claim 11, wherein the power station is a coproduct gas power station and/or the attached $CO_2$-separating power station flue gas treatment plant, is in the form of a $CO_2$ gas scrubber by utilizing an absorbent.

13. The methanation process as claimed in claim 1, wherein the $CO_2$ exhaust gas treatment or $CO_2$ workup is a power station flue gas treatment plant.

14. The methanation process as claimed in claim 1, wherein the combustion chamber of the steam generator, is supplied with the coproduct gas in the form of a gas mixture, containing one or more gaseous byproducts of the smelting works or chemical works as carbonaceous materials stream and fuel.

15. The methanation process as claimed in claim 1, wherein the $CO_2$ is obtained, from the power station flue gas at least partly in the $CO_2$ exhaust gas treatment or the $CO_2$ workup, by utilizing a $CO_2$ gas scrubber with an absorbent.

16. A power station or combustion plant with attached water/steam circuit that comprises a combustion chamber of a steam generator, said chamber being fired with a carbonaceous fuel and said station or plant being designed as an integral constituent of a smelting works or chemical works where the flue gas line of the combustion chamber of the steam generator of the power station or of the combustion plant stands in a line connection, said line connection carrying power station flue gas and/or $CO_2$ obtained therefrom and/or from coproduct gas of the smelting works or chemical works, with a methanation plant or a methanator that reacts said gas to form methane ($CH_4$), wherein the power station or the combustion plant has a line which stands in media-carrying line connection with one or more production-engineering or process-engineering units of the smelting works or chemical works and which supplies a carbonaceous fuel to the combustion chamber of the steam generator of the power station, and via which the combustion chamber of the steam generator can be supplied with a carbonaceous material or materials stream, which comprises one or more byproducts or waste products of the production-engineering or process-engineering units of the smelting works or chemical works, wherein the methanation plant or the methanator stands in at least one heat energy-carrying line connection, said connection at least partly coupling out waste heat arising in the methanation of the flue gas or power station flue gas or $CO_2$ gas, with at least one medium flowing into the combustion chamber of the steam generator of the power station on the burner side, and/or with the water/steam circuit of the power station and/or with a $CO_2$ exhaust gas treatment or $CO_2$ workup connected, in terms of process engineering, upstream of the methanation plant, and/or to one or more production-engineering or process-engineering units of the smelting works or chemical works and hydrogen obtained from the coproduct gas and/or generated utilizing an electrolysis is supplyable to the methanation plant.

17. The power station or combustion plant as claimed in claim 16, wherein the line connection carrying power station flue gas or $CO_2$ gas obtained therefrom comprises a $CO_2$ exhaust gas treatment or $CO_2$ workup, which is connected, in process engineering terms, upstream of the methanation plant or the methanator, and which stands, in the direction of gas flow, on the input side in power station flue gas-supplying line connection with the combustion chamber of the steam generator and, on the output side, in $CO_2$ gas-discharging line connection with the methanation plant or the methanator, and which stands in a heat energy-carrying line connection, said line connection coupling out the waste heat arising in the $CO_2$ exhaust gas treatment or $CO_2$ workup with at least one medium flowing on the burner side to the combustion chamber of the steam generator, and/or with the water/steam circuit of the power station and/or of the methanation plant connected downstream in terms of process engineering, and/or with one or more production-engineering or process-engineering units of the smelting works or chemical works.

18. The power station or combustion plant as claimed in claim 16, wherein the $CO_2$-separating $CO_2$ exhaust gas treatment plant (6) or $CO_2$ workup is designed as a $CO_2$ gas scrubber utilizing an absorbent (PC(C)C =Post-Combustion (Carbon) Capture).

19. The power station or combustion plant as claimed in claim 16 wherein the power station or the combustion plant comprises a generator, which is attached to its water/steam circuit and is driven by a turbo set disposed in the water/steam circuit, said generator standing in power-conducting line connection with the methanation plant or the methanator and/or with the $CO_2$ exhaust gas treatment or the $CO_2$ workup and/or with the electrolysis stands or stand in an excess power-supplying, power-conducting line connection with an attached public power grid.

20. The power station or combustion plant as claimed in claim 16 wherein the carbonaceous material or materials stream with which the power station or the combustion plant can be supplied comprises the one or more byproducts or waste products of the production-engineering or process-engineering units of the smelting works or chemical works in the form of a gas mixture, as carbonaceous fuel in the form of a coproduct gas.

21. The power station or combustion plant as claimed in claim 16 wherein the power station is a coproduct gas power station, which is integrated into a smelting works or chemical works, and the line connection which carries the power station flue gas or $CO_2$ gas obtained therefrom supplies the methanation plant and/or the $CO_2$ exhaust gas treatment or $CO_2$ workup with at least a part of the power station flue gas arising in the combustion of the carbonaceous fuel in the combustion chamber of the steam generator.

22. The power station or combustion plant as claimed in claim 16 wherein said power station or combustion plant is configured to perform a methanation process comprising the conversion of $CO_2$, said methanation process comprising coupling out the heat energy arising as waste heat in the conversion of $CO_2$ to methane in the methanation plant at least partly into the materials stream and/or heat energy stream wherein this stream is supplied at least partly to at least one medium flowing into the combustion chamber of the steam generator of the power station on the burner side and/or to the water/steam circuit of the power station and/or to a $CO_2$ exhaust gas treatment or $CO_2$ workup, which is connected upstream, in terms of process engineering, of the methanation plant, and/or to one or more operating stages of an attached smelting works or chemical works.

23. The power station or combustion plant as claimed in claim 22, wherein the $CO_2$ exhaust gas treatment or $CO_2$ workup is a power station flue gas treatment plant.

24. The power station or combustion plant as claimed in claim 16, wherein the $CO_2$ exhaust gas treatment or $CO_2$ workup is a power station flue gas treatment plant.

25. The power station or combustion plant as claimed in claim 16, wherein the power station is a blast furnace gas power station or a coking plant gas power station.

* * * * *

UNITED STATES PATENT AND TRADEMARK OFFICE
CERTIFICATE OF CORRECTION

PATENT NO. : 10,227,901 B2  
APPLICATION NO. : 14/904033  
DATED : March 12, 2019  
INVENTOR(S) : Christian Bergins et al.

Page 1 of 1

It is certified that error appears in the above-identified patent and that said Letters Patent is hereby corrected as shown below:

In the Specification

In Column 9, Line 39, change "schematicization," to --schematization,--.

In the Claims

In Column 14, Line 43, Claim 1, change "gas of gas of" to --gas of--.

In Column 15, Line 3, Claim 2, change "plat" to --plant--.

In Column 15, Line 58, Claim 11, after "process" insert --as--.

In Column 16, Line 11, Claim 12, after "process" insert --as--.

In Column 16, Line 66, Claim 16, change "supplyable" to --suppliable--.

In Column 17, Line 24, Claim 18, change "(PC(C)C =Post" to --(PC(C)C=Post--.

In Column 18, Line 12 (Approx.), Claim 21, change "$CO_2$workup" to --$CO_2$ workup--.

In Column 18, Line 20 (Approx.), Claim 22, change "$CO_2$to" to --$CO_2$ to--.

Signed and Sealed this  
Third Day of September, 2019

Andrei Iancu  
*Director of the United States Patent and Trademark Office*